United States Patent [19]
Legrand

[11] Patent Number: 5,456,721
[45] Date of Patent: Oct. 10, 1995

[54] DEVICE FOR REINFORCING A LIGAMENT TRANSPLANT DURING RECONSTRUCTIVE SURGERY

[76] Inventor: Jean-Jacques Legrand, 45, allee Jacques-Prevert F-73000, Chambery, France

[21] Appl. No.: 73,536

[22] Filed: Jun. 8, 1993

[51] Int. Cl.[6] .................................. A61F 2/08; A61F 2/02
[52] U.S. Cl. .................... 623/13; 623/1; 623/11
[58] Field of Search .................................. 623/1, 11, 12, 623/13

[56] References Cited

U.S. PATENT DOCUMENTS 4,469,101  9/1984  Coleman et al. ..................... 623/13

FOREIGN PATENT DOCUMENTS 0328401  8/1989  European Pat. Off. .
8204390  12/1982  WIPO .

Primary Examiner—David Isabella
Assistant Examiner—Debra S. Brittingham
Attorney, Agent, or Firm—Lerner, David, Littenberg, Krumholz & Mentlik

[57] ABSTRACT

Device for reinforcing a ligament transplant during reconstructive surgery. The transplant is inserted into a knitted sleeve formed from resorbable yarn, the mesh of which enables said sleeve to be extended in a diamteral direction and includes at one of its ends two loops, which serve to secure said sleeve to one of the insertion points of the transplant. The sleeve can be associated with a tube having an ogival head adapted for sliding into a tractive tube in which the transplant enclosed in the sleeve has been previously placed, the end of the sleeve being passed, by means of a thread-drawing tube, through an opening in the ogival head. The head comprises elastic ribs which can hold onto the body of said tube, the withdrawal of the tractive tube enabling the ribs to be spaced apart and engage the peripheral area of the hole formed in the bone.

16 Claims, 3 Drawing Sheets

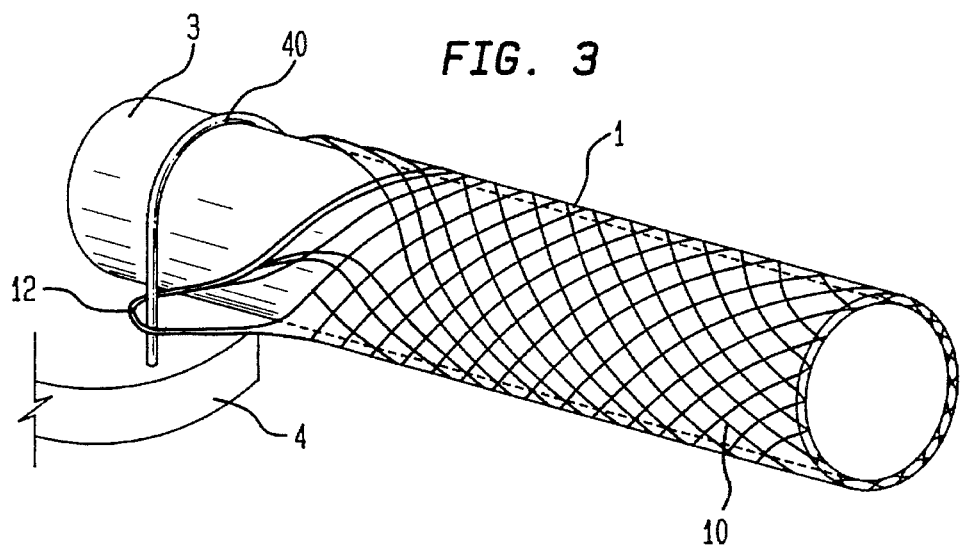
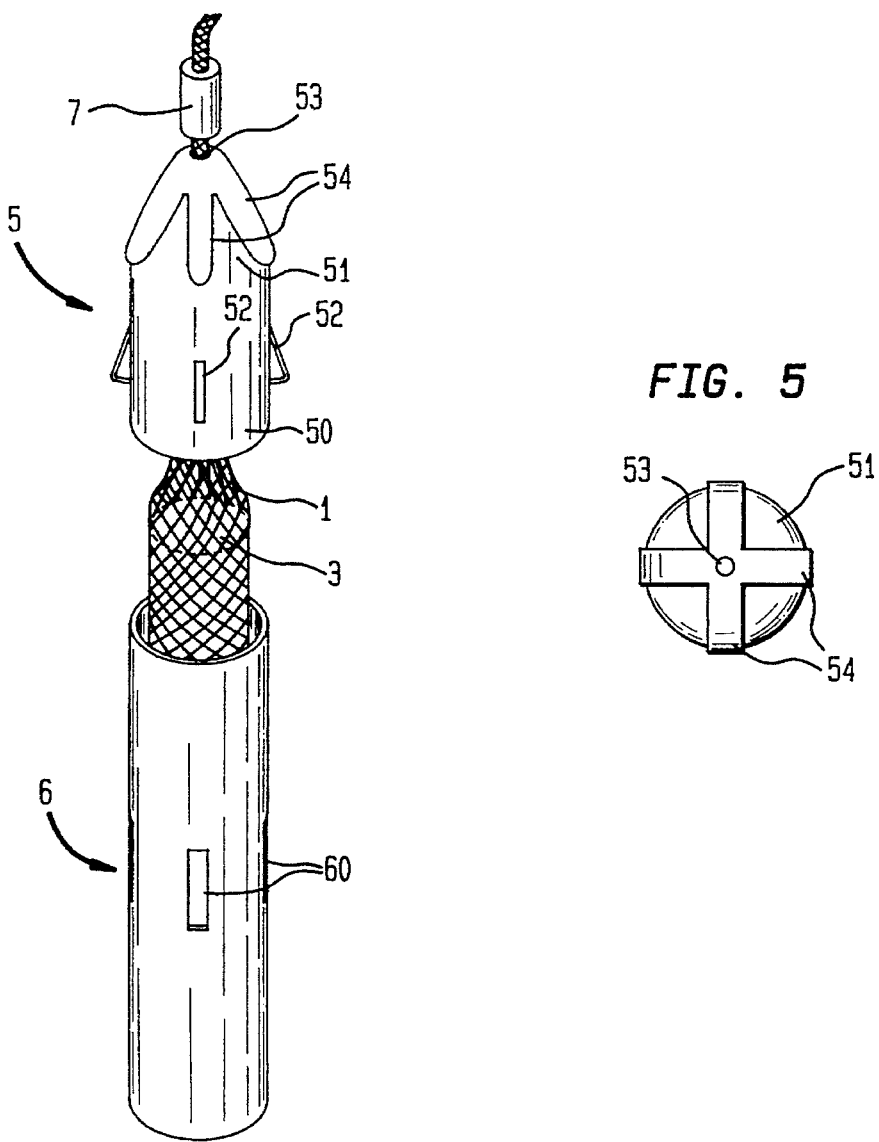

DEVICE FOR REINFORCING A LIGAMENT TRANSPLANT DURING RECONSTRUCTIVE SURGERY

The invention hereto relates to orthopedic surgery and especially to the restoration of articular ligaments.

Lesions of ligaments resulting from car accidents, sport or work, are becoming increasingly frequent.

In most cases, these lesions consist in the rupture of the ligament, and the ligament has to be repaired.

In the case of a recent lesion, a suture and the reinsertion of the ligament with some strengthening device generally help restore the ligament with or without immobilization, depending on the location of the affected joint.

In the case of a late diagnostic, the fragments of ligament retract and suffer some necrosis, making suture impossible and requiring a ligamentoplasty.

A ligamentoplasty may be done either with an artificial or prosthetic ligament, or with an autologous ligament from a transplant tendon or ligament in the immediate area or with a bank tendon taken from a donor's body.

The artificial ligament has the advantages of being easy to install and initially sturdy. Consequently, it does not require any immobilization—which, when needed, may cause a lot of circulation and joints problems—and allows to start reeducation exercises immmediately.

On the other hand, the artificial ligament has some disadvantages due to the materials used, more specifically a risk of rupture and some degree of intolerance. These pitfalls explain why the use of an artificial ligament is rather infrequent.

Surgeons prefer to rely on either autologous ligaments, or tendons and ligaments from a bank. However, to avoid an excessively long immobilization until ligaments are properly anchored and revascularized, which can take 3 to 8 months depending on the location of the joint, the ligament is reinforced either by an artificial ligament—which might lead to tolerance problems—or by resorbable materials, made of lactic acid polymers and/or glycol acid, widely used for suture stitches, and thus well tolerated.

These resorbable materials look like a string or a ribbon. A stripe of ligament is cut out and wrapped across a string or a ribbon made in a resorbable material, then attached at both ends to the insertion points of the ligament being replaced. In the case of a recent lesion, a resorbable ribbon is attached in parallel to the sutured ligament, or tendon, to strengthen it.

However, these strings and ribbons are not well adapted to the role they are required to play: their mechanical properties are indeed different from those of the ligament and the resorbable material; for that reason, the strings and ribbons bridge the forces applied to the joint, and the ligament does not have to work, or very little, so after the resorption of the strings and ribbons, the unused ligament may be strained or fragile.

The apparatus according to the invention hereto is a sheath knitted in a thread made of resorbable material, designed to sheathe the transplant and the bank tendon. The knitting stitch used is one of those known for allowing the sheath to stretch diametrically, while not letting it stretch longitudinally very much once the diameter is set : it is indeed the ability of the transplant to be compressed, and not the thread itself, that gives its elasticity to the transplant sheathed in resorbable material.

In addition, the size of the mesh is designed so as to permit biological exchanges between the transplant or the bank tendon and its environment, bone, synovia, subcutaneous cellular tissues, etc. . .

Finally, the light friction of the sheath massages the transplant or the bank tendon and stimulates its periphery, thus helping the regeneration of fibers oriented in different directions, as necessary for the organ to function properly.

The sheath of resorbable material can be made in different diameters and lengths to match the ligaments of all the articulations. It can also be packaged on an applicator made of a flexible tube, flattened for easy storage along two opposite generants.

In the design according to this Invention, the sheath includes two loops on one end for fixing the sheath, using two suture pins, to one of the insertion points, the other end being clipped with the transplant or the bank tendon to the other insertion point, once the sheath has been adjusted to the required length.

To use the sheath, a simple pressure on the applicator's folds returns the applicator and the sheath to their original cylindrical shape. The transplant or the bank tendon is then inserted into the applicator. After removing the applicator, the end of the sheath without any fixation loop is cut to the required length after simply pulling each end of the sheath until its diameter is adjusted to the transplant or bank tendon diameter.

In the case of a recent lesion, one segment of the ligament or tendon to suture is simply inserted into the resorbable-thread sheath, then the two segments of ligament or tendon are joined together and sutured. The sheath is then slid along the entire sutured ligament or tendon and attached on both ends.

In an other design of the apparatus according to the invention and applicable when a bank tendon must be attached to the bone, as in a procedure involving the transverse ligament of the knee, the sheath is associated with a device helping anchor one of the extremities in a perforation drilled into the bone where the ligament is to be attached.

The device according to this second design includes a cone-shaped head tube, on top of which are attached four ribs that can fold back on the tube's body or open like an umbrella, one end of the sheath which holds the bank tendon being designed to be passed through the tube to a hole made on top of the cone-shaped head, with a knot or a crimping system preventing the sheath and the tendon to slip back.

According to the invention, the top of the cone-shaped head tube includes, below the head, four elastic tabs which are meant to assist the ribs by fastening to the bony walls of the perforation.

The installation of the cone-shaped head tube and of the thread sheath-covered bank tendon in the bone is performed with the help of an inserting tube with four holes for the passage of the tabs of the cone-shaped head tube after the insertion of the cone-shaped head tube and of the sheath-covered tendon into the insertion tube.

The holes of the insertion tube prevent the tabs to be crushed against the inside wall of the insertion tube and avoid a loss of the elasticity they need in order to fasten to the perforation bored into the bone.

The tendon is thus slipped into the thread sheath and the contraption is then inserted into the insertion tube, one end of the sheath protruding on the side of the upper portion of the insertion tube, where the passage holes of the tabs of the cone-headed shape tube are located.

This end of the sheath is then inserted into a small threading tube, which helps it pass through the hole located on the top of the cone-shaped head tube. The threading tube is then removed and the end of the sheath protruding from the top of the cone-shaped head is tied to prevent any retraction.

The growth of the bone will allow to colonize the pieces inserted in the orifice, assuring that the bank tendon stays in place after resorption of the thread sheath.

This device has additional uses in urology, gynecology and gastroenterology, for example help remedy prolapsus by using bank tendons reinforced by sheaths according to the invention, as a mean to better support the organs.

The advantages and the feature of the invention hereto will appear more clearly in the following description and in the related drawings which represent only one possible type of design.

In the appended drawings:

FIG. 3 shows a partial view in perspective of a way to attach the transplant or the bank tendon and the sheath to an insertion point of the ligament.

FIG. 4 shows a view in perspective of the fastening and inserting device.

FIG. 5 shows a top view of the cone-shaped head tube.

FIG. 1 shows that the strengthening device of ligaments according to the invention is knitted with a thread 10 of resorbable material. The mesh 11, of a known type, allows the sheath to stretch diametrically, while stretching very little longitudinally once the diameter is set.

On one end of the sheath 1 are attached two loops 12, either from an extension of the thread 10 used to make the above-mentioned sheath, or made of a separate thread, also in resorbable material, securely attached to the sheath 1.

Figure 1:
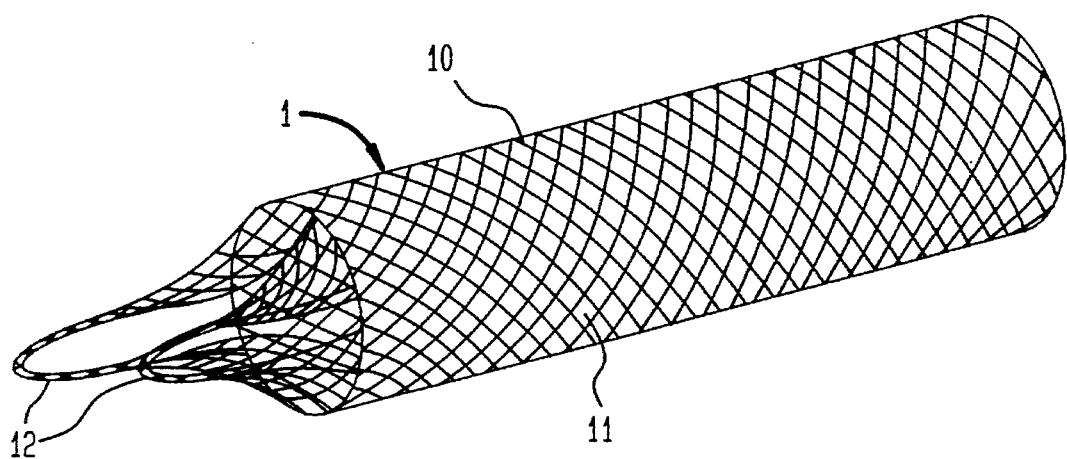
FIG. 1 shows a view in perspective of a strengthening sheath made in resorbable thread according to the invention.
Figure 2A:
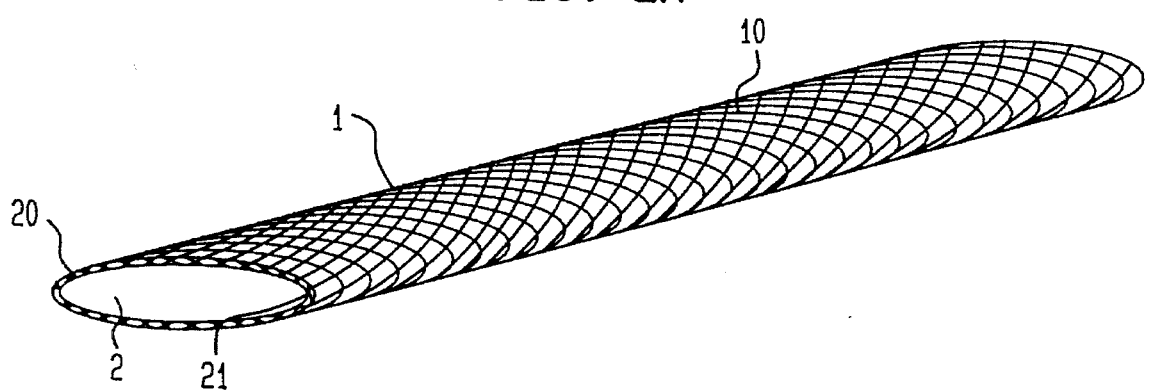
FIG. 2A shows a partial view in perspective of the same sheath slipped on an applicator.
Figure 2B:
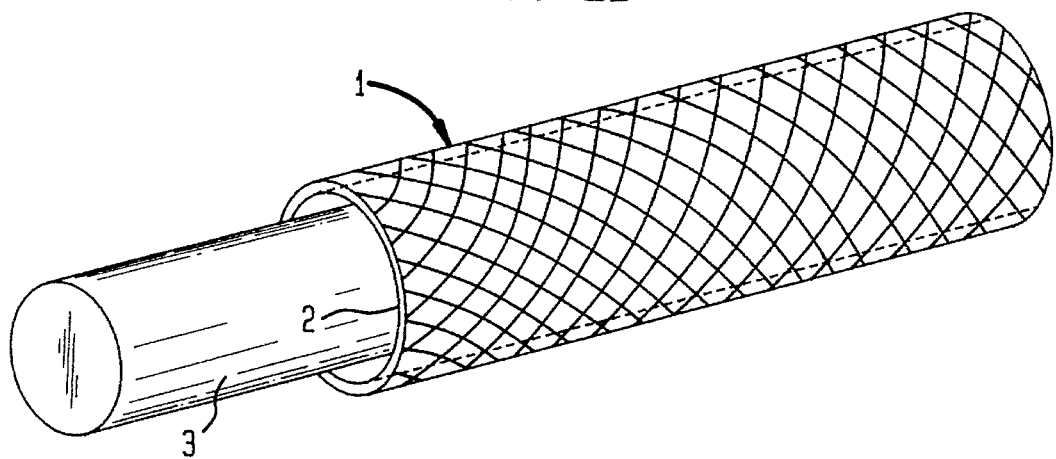
FIG. 2b shows a partial view in perspective of the same sheath and of the same applicator in which a transplant or a bank tendon is being inserted.

FIG. 2b shows that the sheath 1 can be packaged over an applicator 2 made of a relatively flexible tube flattened along two opposite generants and creating two folds 20 and 21.

FIG. 2b shows that after pushing on the applicator 2 in the proximity of the folds 20 and 21, the applicator 2 and the sheath 1 return to their original cylindrical shape, and it is then possible to insert the transplant or the bank tendon 3 into the applicator 2, so that after removal of the applicator 2, the transplant or the bank tendon 3 is inside the sheath 1, the pulling on both ends of the sheath 1 enabling to adjust its diameter to the diameter of the transplant or the bank tendon 3.

FIG. 3 shows how the transplant or bank tendon 3, covered with the sheath 1, is attached to the bone 4 of the articulation with a sin 40 securely holding the transplant or bank tendon 3 and the loops 12 of the sheath 1.

It is also possible to attach the device with several clips, one holding the transplant or bank tendon 3 and the two others fixing one of the loops 12 of the sheath 1 on each side of the said transplant or bank tendon 3.

FIG. 4 shows a bank tendon slipped into a thread sheath 1, both of them having been subsequently inserted in the insertion tube 6.

The extremity of the sheath 1 has been passed into a threading tube 7 before being inserted into the cone-shaped head 51 tube 5, to help it pass through the hole 53 of the cone-shaped head. The threading tube 7 will later be removed and the extremity of the sheath 1 will be tied to prevent it from retracting through the hole 52.

In addition, the cone-shaped head 51 includes ribs 54 attached by one end around the hole 52 which are somewhat elastic. The body 50 of the tube 5 includes, on its upper portion and below the cone-shaped head 51, four retractable tabs 52 aligned with the ribs 54.

The cone-shaped head 51 tube 5 is then inserted into the insertion tube 6 until the four tabs 52 snap into place in the holes 60 of the insertion rude 6, the ribs 54 being kept folded by the insertion tube 6.

FIG. 5 shows a top view of the cone-shaped head 51, with the hole 53 and the four ribs 54 positioned in the shade of a cross, their base being fixed around the above-mentioned hole.

Figure 6:
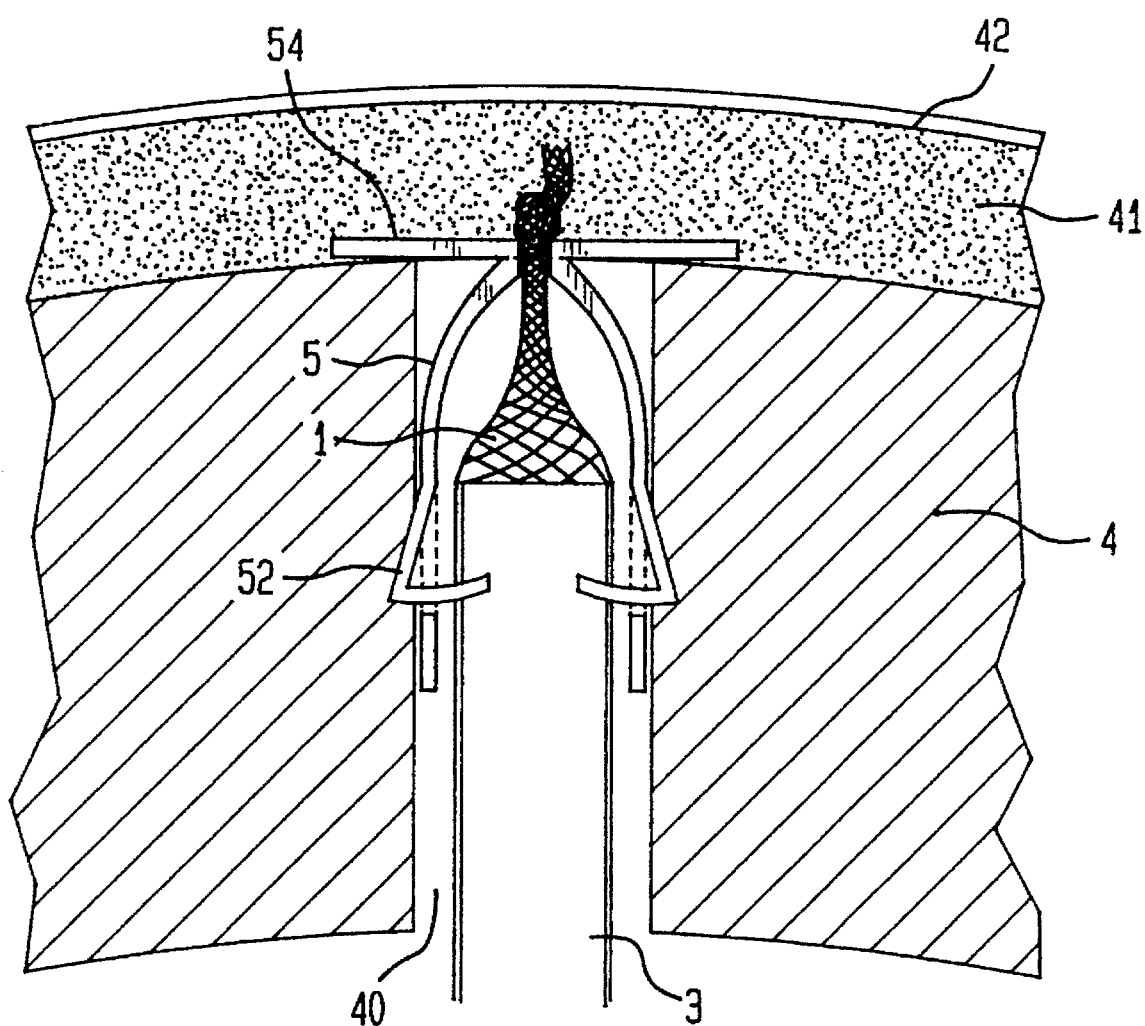
FIG. 6 shows a simplified cross-sectional view of the cone-shaped head tube installed on a bone.

FIG. 6 shows a tube 5 inserted in a perforation 40 bored into a knee borne during a procedure involving the transverse ligament of the knee.

One may note that the orifice 40 has not been made from the skin 42 directly above the bone 4, but from another point.

The advantage of this method is that the procedure requires only one incision instead of two or three required by current procedures.

The installation of the cone-shaped head 51 tube 5 and of the bank tendon 3 covered with the sheath 1 is performed by inserting the insertion tube 6 into the perforation 40 bored into the bone 4.

After inserting the insertion tube 6 in the hole 40, that tube only has to be removed to release the ribs 54 and the tabs 54 and the said ribs and tabs can then spread thanks of their elasticity, and lean on the bony wall strengthening the attachment of the tendon 3.

By pulling on the sheath 3, the tabs 52 fasten to the bony wall of the orifice 40 and assist the ribs 54, their free extremities helping also to anchor the tendon, and reducing the stress on the knot or crimping at the extremity 1 of the sheath 3.

The cone-shaped head tube 5 can be made in metal or in polyethylene.

In addition, a piece of bone can be left at the end of the bank tendon or of the transplant to make the bone growth and the anchoring of the tendon or transplant easier.

I claim:

1. A device of use during surgery, comprising:

a sheath having an original diameter and including resorbable material made of knitted elastic threads adapted to permit said sheath to expand beyond its original diameter, said knitted threads defining a predetermined mesh size so that biological exchanges can take place between an associated ligament used to replace a damaged ligament of a patient and the surrounding biological environment within the patient's body; applicator means including a flexible tube for applying said sheath onto a replacement ligament, said sheath being mountable on said flexible tube and being movable from its mounted position on said flexible tube to the replacement ligament; and anchoring means for anchoring said sheath within a passageway through a bone, said anchoring means including a second tube having a conical head, said sheath extending through said second tube and said conical head and being secured to said conical head.

2. The device of claim 1 wherein said flexible tube has a tubular configuration and is resilient such that it may be compressed to a generally flattened configuration and may thereafter resume its original tubular configuration.

3. The device of claim 1 further comprising loop means attached to said sheath for permitting said sheath to be placed in association with securing means so that it can be secured to a bone.

4. The device of claim 1 wherein said conical head comprises an aperture therein through which said sheath extends so that said sheath can be secured thereto.

5. The device of claim 4 further comprising threading means for facilitating threading of said sheath through said aperture of said conical head.

6. The device of claim 5 wherein said threading means comprises a threading tube, said sheath being arranged within said threading tube and being removably attached thereto so that said threading tube can be removed after said sheath is placed through said aperture of said conical head.

7. The device of claim 4 wherein said second tube comprises a plurality of elastic ribs arranged on an external surface of said conical head for facilitating mounting of the device on a bone.

8. The device of claim 7 wherein said plurality of elastic ribs are movable between a first position at which said ribs are arranged adjacent the external surface of said second tube and an extended position at which said plurality of ribs are arranged adjacent an associated bone on which it is mounted.

9. The device of claim 1 wherein said second tube comprises a plurality of elastic tabs arranged on the external surface thereof so that mounting of the device within an associate bone is enhanced.

10. The device of claim 9 further comprising insertion tube means for inserting said second tube and said sheath into a passageway within a bone, said second tube being removably mounted in said insertion tube so that said insertion tube can be removed from the passageway of the bone after said second tube and said sheath are placed therein.

11. The device of claim 9 wherein said insertion tube means comprises a plurality of spaced apertures arranged for alignment with said plurality of elastic tabs of said second tube so that said plurality of tabs can be removably mounted within corresponding ones of said plurality of apertures when said second tube is mounted on said insertion tube means.

12. A device for use during surgery, comprising:

a sheath having an original diameter and including resorbable material made of knitted elastic threads adapted to permit said sheath to expand beyond its original diameter, said knitted threads defining a predetermined mesh size selected so that biological exchanges can take place between an associated ligament used to replace a damaged ligament of a patient and the surrounding biological environment within the patient's body; applicator means including a flexible tube for applying said sheath onto a replacement ligament, said sheath being mountable on said flexible tube and being movable from its mounted position on said flexible tube to the replacement ligament; and anchoring means for anchoring said sheath within a passageway through a bone, said anchoring means including a second tube having a conical head, said sheath extending through said second tube and said conical head and being secured to said conical head, said second tube comprising a plurality of elastic ribs arranged on an external surface of said conical head for facilitating mounting of the device on a bone, said second tube further comprising a plurality of elastic tabs arranged on the external surface thereof so that mounting of the device within an associated bone is enhanced.

13. The device of claim 12 further comprising insertion tube means for inserting said second tube and said sheath into a passageway within a bone, said second tube being removably mounted on said insertion tube so that said insertion tube can be removed from the passageway of the bone after said second tube and said sheath are placed therein.

14. The device of claim 13 wherein said insertion tube means comprises a plurality of spaced apertures arranged for alignment with said plurality of elastic tabs of said second tube so that said plurality of elastic tabs can be removably mounted within corresponding ones of said plurality of apertures when said second tube is mounted on said insertion tube means.

15. The device of claim 12 wherein said conical head comprises an aperture through which said sheath extends so that said sheath can be secured thereto, said device further comprises threading means for facilitating threading of said sheath through said aperture of said conical head, said threading means comprising a threading tube, said sheath being arranged within said threading tube and being removably attached thereto so that said threading tube can be removed after said sheath is placed through said aperture of said conical head.

16. The device of claim 12 wherein said flexible tube originally has a tubular configuration and is resilient so that it may be compressed to a generally flattened configuration and may thereafter resume its original tubular configuration.

* * * * *

UNITED STATES PATENT AND TRADEMARK OFFICE
CERTIFICATE OF CORRECTION

PATENT NO. : 5,456,721
DATED : October 10, 1995
INVENTOR(S) : Legrand

It is certified that error appears in the above-indentified patent and that said Letters Patent is hereby corrected as shown below:

```
Column 2, line 9, "Invention" should read --invention--.
Column 3, line 51 "sin" should read --pin--.
Column 3, line 65, "52" should read --53--.
Column 3, line 67, "52" should read --53--.
Column 4, line 6, "rude" should read --tube--.
Column 4, line 9, "shade" should read --shape--.
Column 4, line 13, "borne" should read --bone--.
Column 4, line 59, "flexibe tube has" should read --flexible tube originally has--.
Column 4, line 60, "such" should read --so--.
Column 5, line 11, "4" should read --1--.
```

Signed and Sealed this

Ninth Day of January, 1996

BRUCE LEHMAN

Attest:

Attesting Officer

Commissioner of Patents and Trademarks